United States Patent
Smith et al.

(10) Patent No.: US 10,925,317 B2
(45) Date of Patent: Feb. 23, 2021

(54) ELECTRONIC SMOKING DEVICE WITH CAVITY FOR LIQUID RESERVOIR

(71) Applicant: Fontem Holdings 1 B.V., Amsterdam (NL)

(72) Inventors: Simon James Smith, Cambridge (GB); David William Drury Harrison, Cambridge (GB); Alexander Edward Muir, Cambridge (GB); Hitesh Bagai, Bristol (GB)

(73) Assignee: Fontem Holdings 1 B.V., Amsterdam (NL)

( * ) Notice: Subject to any disclaimer, the term of this patent is extended or adjusted under 35 U.S.C. 154(b) by 347 days.

(21) Appl. No.: 15/775,738

(22) PCT Filed: Nov. 10, 2016

(86) PCT No.: PCT/EP2016/077302
§ 371 (c)(1),
(2) Date: May 11, 2018

(87) PCT Pub. No.: WO2017/081176
PCT Pub. Date: May 18, 2017

(65) Prior Publication Data
US 2018/0368475 A1 Dec. 27, 2018

(30) Foreign Application Priority Data
Nov. 12, 2015 (EP) .................................. 15194308

(51) Int. Cl.
*A24F 13/00* (2006.01)
*A24F 17/00* (2006.01)
(Continued)

(52) U.S. Cl.
CPC ............ *A24F 47/008* (2013.01); *A24F 40/42* (2020.01); *A61M 11/042* (2014.02);
(Continued)

(58) Field of Classification Search
CPC .... A24F 15/015; A24F 47/002; A24F 47/008; A24F 40/42
(Continued)

(56) References Cited

U.S. PATENT DOCUMENTS 10,426,195 B2 * 10/2019 Bagai ........................ H05B 3/00
10,440,997 B2 * 10/2019 Borkovec ......... A61M 15/0028
(Continued)

FOREIGN PATENT DOCUMENTS

CN 2513025 Y 9/2002
CN 2539534 Y 3/2003
(Continued)

*Primary Examiner* — Hae Moon Hyeon
(74) *Attorney, Agent, or Firm* — Dykema Gossett PLLC (57) ABSTRACT

An electronic smoking device (210, 310, 410) has two portions (12, 13) wherein one of the portions (12, 13) comprises a cavity (240, 340, 440) for a liquid reservoir (234, 334, 434). The portions (12, 13) can be moved with respect to each other, by a movement and a respective counter movement, at least between an insertion configuration and a closed cavity configuration. In the insertion configuration a liquid reservoir (234, 334, 434) can be inserted into the cavity (340, 440). In a closed cavity configuration, the cavity (240, 340, 440) is closed by the other portion and a liquid reservoir opening element (70) of said one or the other portion opens the housed liquid reservoir (234, 334, 434).

12 Claims, 6 Drawing Sheets

(51) Int. Cl.

| | | |
|---|---|---|
| *A24F 25/00* | (2006.01) | |
| *A24F 47/00* | (2020.01) | |
| *A61M 15/06* | (2006.01) | |
| *A61M 15/00* | (2006.01) | |
| *A61M 11/04* | (2006.01) | |
| *A24F 40/42* | (2020.01) | |
| *A61M 16/00* | (2006.01) | |

(52) U.S. Cl.
CPC ...... *A61M 15/003* (2014.02); *A61M 15/0023* (2014.02); *A61M 15/06* (2013.01); *A61M 15/0035* (2014.02); *A61M 15/0063* (2014.02); *A61M 2016/0018* (2013.01); *A61M 2205/3653* (2013.01); *A61M 2205/582* (2013.01); *A61M 2205/583* (2013.01); *A61M 2205/6045* (2013.01); *A61M 2205/8206* (2013.01)

(58) Field of Classification Search
USPC .................................................. 131/329, 328
See application file for complete search history.

(56) References Cited

U.S. PATENT DOCUMENTS

| | | | |
|---|---|---|---|
| 2007/0076067 A1 | 4/2007 | Hamano et al. | |
| 2009/0151717 A1 | 6/2009 | Bowen et al. | |
| 2013/0125906 A1* | 5/2013 | Hon | H05B 3/42 |
| | | | 131/329 |
| 2014/0251357 A1 | 9/2014 | Tritz et al. | |
| 2014/0338680 A1* | 11/2014 | Abramov | A24F 47/008 |
| | | | 131/328 |
| 2014/0338685 A1 | 11/2014 | Amir | |
| 2015/0090253 A1* | 4/2015 | Farrow | A61M 15/06 |
| | | | 128/200.14 |
| 2015/0305406 A1* | 10/2015 | Li | A24F 47/008 |
| | | | 131/329 |
| 2016/0007648 A1* | 1/2016 | Sutton | A24F 13/06 |
| | | | 131/187 |
| 2016/0021933 A1* | 1/2016 | Thorens | A24F 47/008 |
| | | | 131/329 |
| 2016/0029699 A1* | 2/2016 | Li | A24F 47/008 |
| | | | 131/329 |
| 2016/0095356 A1* | 4/2016 | Chan | H05B 3/44 |
| | | | 131/329 |
| 2016/0120222 A1* | 5/2016 | Bagai | H05B 3/00 |
| | | | 131/329 |
| 2016/0150828 A1* | 6/2016 | Goldstein | A24F 47/008 |
| | | | 392/387 |
| 2017/0006917 A1* | 1/2017 | Alvarez | A61M 15/06 |
| 2017/0231286 A1* | 8/2017 | Borkovec | A61M 15/06 |
| | | | 131/329 |

FOREIGN PATENT DOCUMENTS

| | | |
|---|---|---|
| CN | 103960785 A | 8/2014 |
| CN | 103974635 A | 8/2014 |
| CN | 104248043 A | 12/2014 |
| WO | 2014/110119 A1 | 7/2014 |
| WO | 2014116974 A1 | 7/2014 |
| WO | 2015/117700 A1 | 8/2015 |

* cited by examiner

ELECTRONIC SMOKING DEVICE WITH CAVITY FOR LIQUID RESERVOIR

CROSS-REFERENCE TO RELATED APPLICATIONS

This application is a United States national stage application of International application no. PCT/EP2016/077302, filed 10 Nov. 2016 (the '302 application) and published under International publication no. WO 2017/081176 on 18 May 2017. This application claims priority to European application no. 15194308.1, filed 12 Nov. 2015 (the '308 application) and granted under European patent no. EP3167728 on 15 Apr. 2020. The '302 application and the '308 application are both hereby incorporated by reference as though fully set forth herein.

FIELD OF INVENTION

The present invention relates generally to electronic smoking devices and in particular electronic cigarettes.

BACKGROUND OF THE INVENTION

An electronic smoking device, such as an electronic cigarette (e-cigarette), typically has a housing accommodating an electric power source (e.g. a single use or rechargeable battery, electrical plug, or other power source), and an electrically operable atomizer. The atomizer vaporizes or atomizes liquid supplied from a reservoir and provides vaporized or atomized liquid as an aerosol. Control electronics control the activation of the atomizer. In some electronic cigarettes, an airflow sensor is provided within the electronic smoking device, which detects a user puffing on the device (e.g., by sensing an under-pressure or an air flow pattern through the device). The airflow sensor indicates or signals the puff to the control electronics to power up the device and generate vapor. In other e-cigarettes, a switch is used to power up the e-cigarette to generate a puff of vapor.

SUMMARY OF THE INVENTION

In accordance with one aspect of the present invention, an electronic smoking device is provided. The device comprises at least two portions which can be moved with respect to each other by a movement and a respective counter movement. One of the portions comprises a cavity configured for at least partly housing a liquid reservoir. The at least two portions can be moved at least between an insertion configuration and a closed cavity configuration. In the insertion configuration, a liquid reservoir can be inserted into the cavity. In the closed cavity configuration, the other portion closes the cavity and a liquid reservoir opening element comprised by said one or the other portion opens the housed liquid reservoir.

The characteristics, features and advantages of this invention and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, same element numbers indicate same elements in each of the views.

DESCRIPTION OF THE PREFERRED EMBODIMENTS

Figure 1:
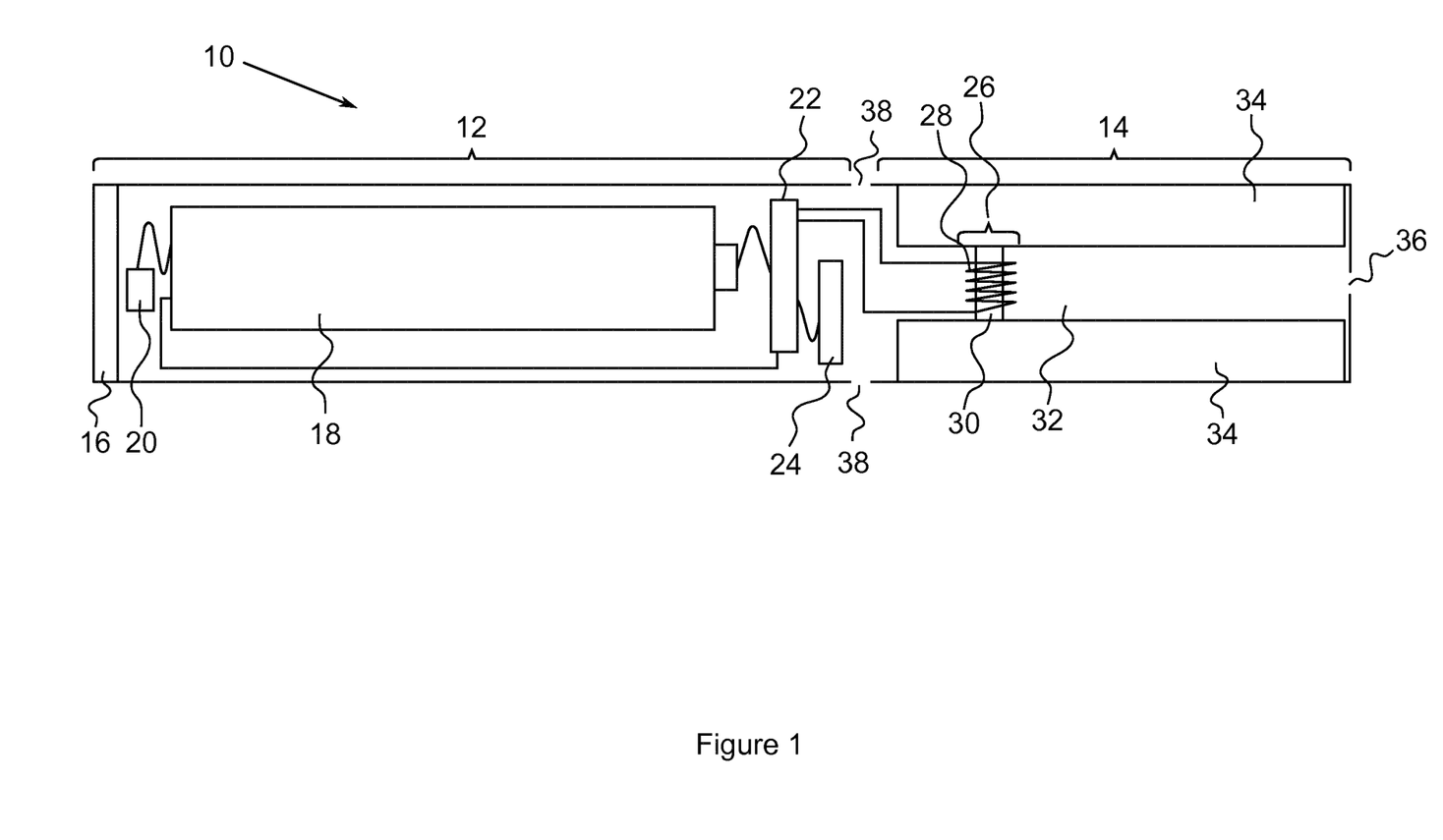
FIG. 1 is a schematic cross-sectional illustration of an exemplary e-cigarette.

Throughout the following, an electronic smoking device will be exemplarily described with reference to an e-cigarette. As is shown in FIG. 1, an e-cigarette 10 typically has a housing comprising a cylindrical hollow tube having an end cap 16. The cylindrical hollow tube may be a single-piece or a multiple-piece tube. In FIG. 1, the cylindrical hollow tube is shown as a two-piece structure having a battery portion 12 and an atomizer/liquid reservoir portion 14. Together the battery portion 12 and the atomizer/liquid reservoir portion 14 form a cylindrical tube which can be approximately the same size and shape as a conventional cigarette, typically about 100 mm with a 7.5 mm diameter, although lengths may range from 70 to 150 or 180 mm, and diameters from 5 to 20 mm.

The battery portion 12 and atomizer/liquid reservoir portion 14 are typically made of metal, e.g. steel or aluminum, or of hardwearing plastic and act together with the end cap 16 to provide a housing to contain the components of the e-cigarette 10. The battery portion 12 and an atomizer/liquid reservoir portion 14 may be configured to fit together by a friction push fit, a snap fit, or a bayonet attachment, magnetic fit, or screw threads. The end cap 16 is provided at the front end of the battery portion 12. The end cap 16 may be made from translucent plastic or other translucent material to allow a light-emitting diode (LED) 20 positioned near the end cap to emit light through the end cap. The end cap can be made of metal or other materials that do not allow light to pass.

An air inlet may be provided in the end cap, at the edge of the inlet next to the cylindrical hollow tube, anywhere along the length of the cylindrical hollow tube, or at the connection of the battery portion 12 and the atomizer/liquid reservoir portion 14. FIG. 1 shows a pair of air inlets 38 provided at the intersection between the battery portion 12 and the atomizer/liquid reservoir portion 14.

A battery 18, an LED 20, control electronics 22 and optionally an airflow sensor 24 are provided within the cylindrical hollow tube battery portion 12. The battery 18 is electrically connected to the control electronics 22, which are electrically connected to the LED 20 and the airflow sensor 24. In this example the LED 20 is at the front end of the battery portion 12, adjacent to the end cap 16 and the control electronics 22 and airflow sensor 24 are provided in the central cavity at the other end of the battery 18 adjacent the atomizer/liquid reservoir portion 14.

The airflow sensor 24 acts as a puff detector, detecting a user puffing or sucking on the atomizer/liquid reservoir portion 14 of the e-cigarette 10. The airflow sensor 24 can be any suitable sensor for detecting changes in airflow or air pressure, such as a microphone switch including a deformable membrane which is caused to move by variations in air pressure. Alternatively the sensor may be a Hall element or an electro-mechanical sensor.

The control electronics 22 are also connected to an atomizer 26. In the example shown, the atomizer 26 includes a heating coil 28 which is wrapped around a wick 30 extending across a central passage 32 of the atomizer/liquid reservoir portion 14. The coil 28 may be positioned anywhere in the atomizer 26 and may be transverse or parallel to the liquid reservoir 34. The wick 30 and heating coil 28 do not completely block the central passage 32. Rather an air gap is provided on either side of the heating coil 28 enabling air to flow past the heating coil 28 and the wick 30. The atomizer may alternatively use other forms of heating elements, such as ceramic heaters, or fiber or mesh material heaters. Nonresistance heating elements such as sonic, piezo and jet spray may also be used in the atomizer in place of the heating coil.

The central passage 32 is surrounded by a cylindrical liquid reservoir 34 with the ends of the wick 30 abutting or extending into the liquid reservoir 34. The wick 30 may be a porous material such as a bundle of fiberglass fibers, with liquid in the liquid reservoir 34 drawn by capillary action from the ends of the wick 30 towards the central portion of the wick 30 encircled by the heating coil 28.

The liquid reservoir 34 may alternatively include wadding soaked in liquid which encircles the central passage 32 with the ends of the wick 30 abutting the wadding. In other embodiments the liquid reservoir 34 may comprise a toroidal cavity arranged to be filled with liquid and with the ends of the wick 30 extending into the toroidal cavity.

An air inhalation port 36 is provided at the back end of the atomizer/liquid reservoir portion 14 remote from the end cap 16. The inhalation port 36 may be formed from the cylindrical hollow tube atomizer/liquid reservoir portion 14 or maybe formed in an end cap.

In use, a user sucks on the e-cigarette 10. This causes air to be drawn into the e-cigarette 10 via one or more air inlets, such as air inlets 38, and to be drawn through the central passage 32 towards the air inhalation port 36. The change in air pressure which arises is detected by the airflow sensor 24, which generates an electrical signal that is passed to the control electronics 22. In response to the signal, the control electronics 22 activate the heating coil 28, which causes liquid present in the wick 30 to be vaporized creating an aerosol (which may comprise gaseous and liquid components) within the central passage 32. As the user continues to suck on the e-cigarette 10, this aerosol is drawn through the central passage 32 and inhaled by the user. At the same time the control electronics 22 also activate the LED 20 causing the LED 20 to light up which is visible via the translucent end cap 16 mimicking the appearance of a glowing ember at the end of a conventional cigarette. As liquid present in the wick 30 is converted into an aerosol, more liquid is drawn into the wick 30 from the liquid reservoir 34 by capillary action and thus is available to be converted into an aerosol through subsequent activation of the heating coil 28.

The battery 18 is rechargeable or replaceable. Further, the liquid reservoir of the e-cigarette 10 is replaceable by a new liquid reservoir 34 thereby replenishing the supply of liquid. In some cases, replacing the liquid reservoir 34 may involve replacement of the heating coil 28 and the wick 30 along with the replacement of the liquid reservoir 34. A replaceable unit comprising the atomizer 26 and the liquid reservoir 34 is called a cartomizer. In some other embodiments the liquid reservoir of the e-cigarette 10 is replaceable independently from the atomizer which may or may not be separately detachable.

The new liquid reservoir 34 may be in the form of a cartridge having a central passage 32 through which a user inhales aerosol. In other embodiments, aerosol may flow around the exterior of the cartridge 32 to an air inhalation port 36.

Of course, in addition to the above description of the structure and function of a typical e-cigarette 10, variations also exist. For example, the LED 20 may be omitted. The airflow sensor 24 may be placed adjacent the end cap 16 rather than in the middle of the e-cigarette. The airflow sensor 24 may be replaced with a switch which enables a user to activate the e-cigarette manually rather than in response to the detection of a change in air flow or air pressure.

Different types of atomizers may be used. Thus, for example, the atomizer may have a heating coil in a cavity in the interior of a porous body soaked in liquid. In this design, aerosol is generated by evaporating the liquid within the porous body either by activation of the coil heating the porous body or alternatively by the heated air passing over or through the porous body. Alternatively the atomizer may use a piezoelectric atomizer to create an aerosol either in combination or in the absence of a heater.

Figure 2:
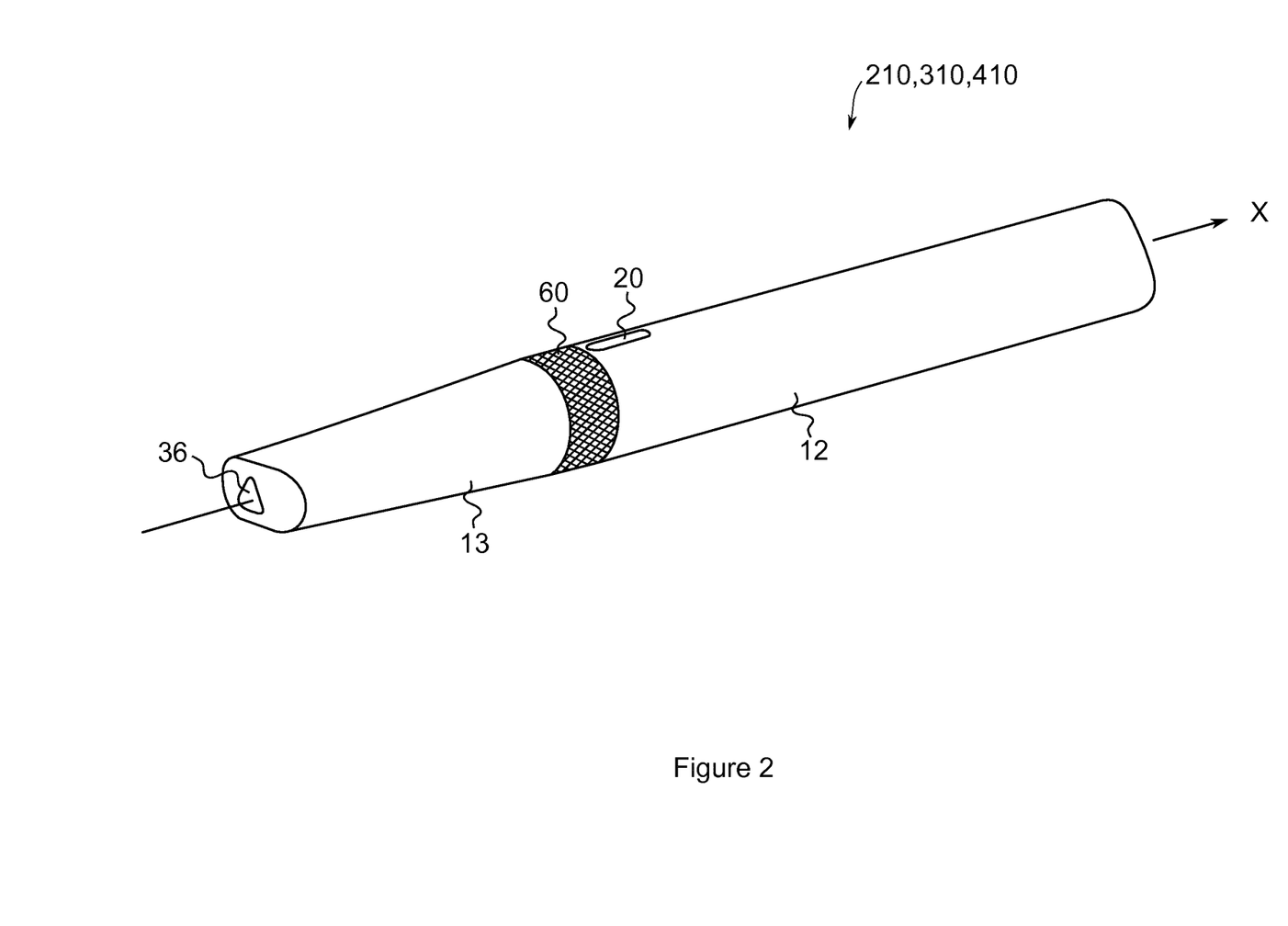
FIG. 2 shows a schematic depicting of an exemplary electronic smoking device according to an aspect of the invention.
Figure 3:
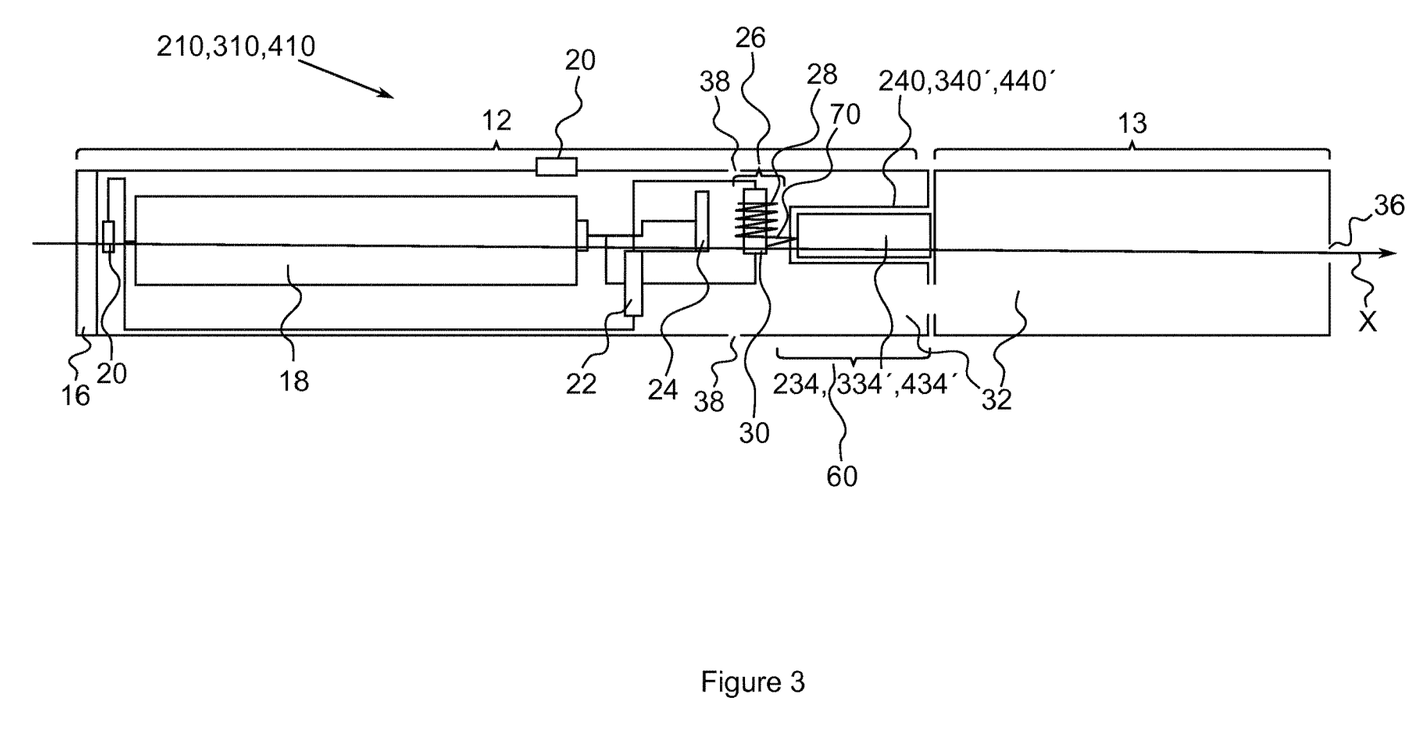
FIG. 3 is a schematic cross-sectional illustration of the exemplary electronic smoking device shown in FIG. 2.

As is shown in FIGS. 2 and 3, an electronic smoking device 210, 310, 410 according to an aspect of the invention has two portions 12, 13, a battery portion 12 for comprising a battery and a mouthpiece portion 13 having an inhalation port 36. A heating coil 28 is arranged in a central passage of the electronic smoking device 210, 310, 410. The central passage connects an air inlet port 38 of the electronic smoking device 210, 310, 410 with the inhalation port 36. The electronic smoking device 210, 310, 410 has an LED 20 which is optional. The LED 20 can be used for signaling low battery and/or operation of the device, for instance. Optionally, the LED 20 is arranged such that it can be viewed through a translucent insert. Then, the translucent insert can optionally have functionality of a switch for instance for switching pre-heating and/or boosting of heating by the heating coil 28. The portions 12, 13 can be moved with respect to each other, by a movement and a respective counter movement, at least between an insertion configuration and a closed cavity configuration. In the closed cavity configuration, the two portions 12, 13 are aligned along a main axis X of the electronic smoking device 210, 310, 410. One of the portions comprises a cavity 240, 340, 440 configured for at least partly housing a liquid reservoir 234, 334, 434.

If only a part is housed by the cavity, a remaining part of the liquid reservoir can be housed in a further cavity comprised by the other portion. The cavity and/or the further cavity comprise at least one one-way fit element which allows for insertion of the liquid reservoir in a relative orientation and prevents insertion of the liquid reservoir into the cavity in an opposite orientation. The one-way fit element is optional however and can be left out without departing from the scope of the invention.

The battery portion 12 of electronic smoking device 210, 310, 410 has a rotatable part 60 with a knurled surface wherein the rotatable part 60 and/or the knurled surface is optional however and can be left out without departing from the scope of the invention. The knurled surface provides a user with a haptic feedback and indicates, in the closed cavity configuration, where the portions 12, 13 adjoin. In some embodiments the movement comprises a twisting of the rotatable part 60 of the battery portion 12 with respect to the mouthpiece portion 13. Then the closed cavity configuration can be such that the battery portion 12 and the mouthpiece portion 13 are locked by a tight locking thread, a loose spiral with end stop notch or the like. This enables a feedback when the device is closed and/or locked.

Figure 4:
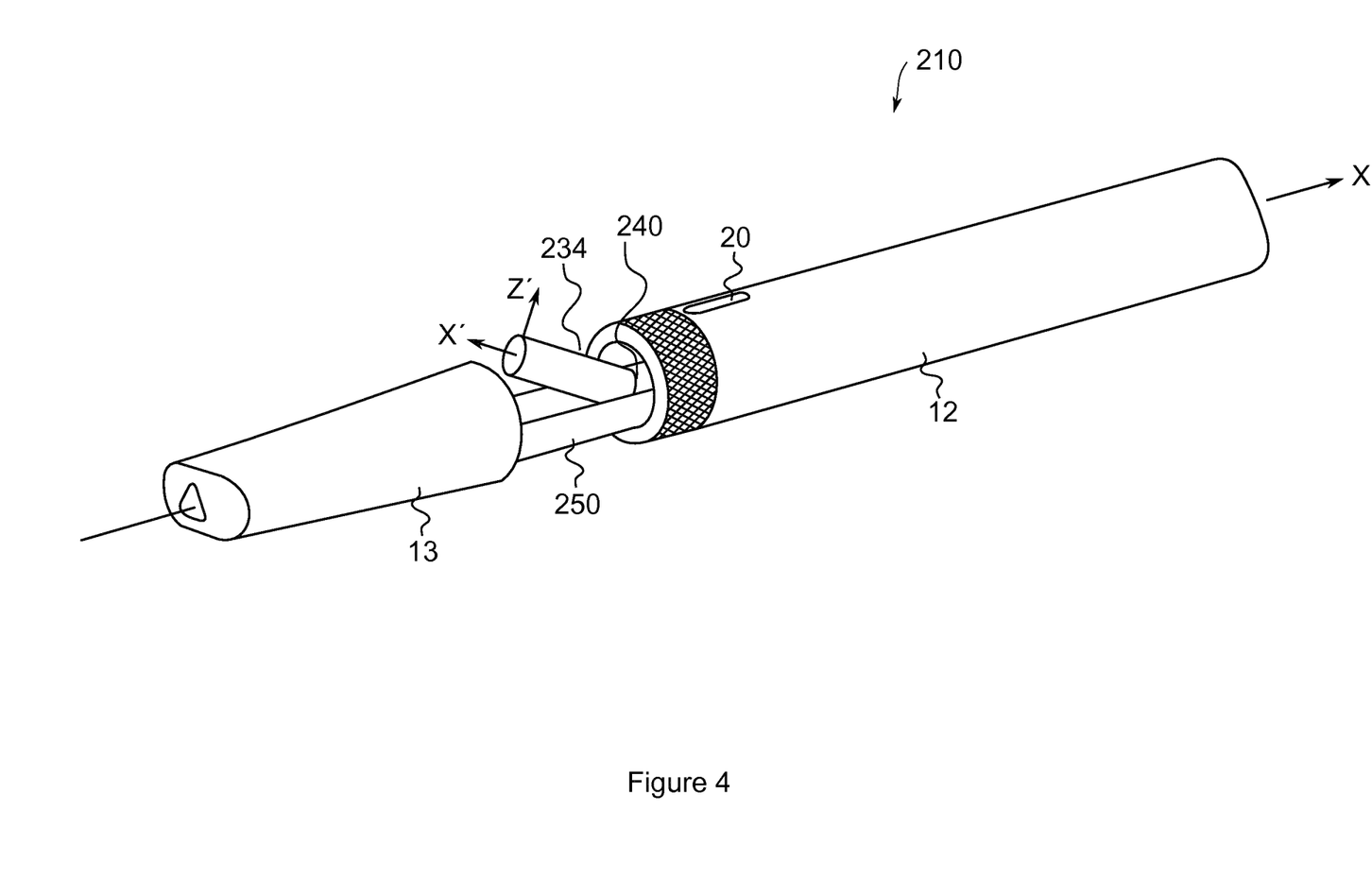
FIG. 4 shows a schematic depicting of an exemplary embodiment of an electronic smoking device according to an aspect of the invention.

An electronic smoking device 210 according to an exemplary embodiment of the invention is shown in FIG. 4 in the insertion configuration. The electronic smoking device 210 has a tray 250. A liquid reservoir 234 (also called capsules) can be laid on the tray in the insertion configuration and the movement comprises a linear movement along the main axis X and the counter-movement comprises a linear counter-movement along the main axis X. By the linear movement, the cavity is opened and the tray 250 is slid out of a cavity of the battery portion 12.

The linear counter-movement slides the tray 250 into a cavity 240 of the battery portion 12 and closes the cavity 240 by the mouthpiece portion 13. Additionally, a liquid reservoir opening element (not shown in FIG. 4, e.g. a piercing pin) is pressed either by the linear counter-movement against the liquid reservoir 234 housed in the cavity 240 thereby opening, e.g. piercing or perforating, the liquid reservoir 234. Or, the linear counter-movement only slides the tray 250 into the cavity 240 of the battery portion 12 and closes the cavity 240 by the mouthpiece portion 13. Then, the counter-movement further comprises a twist movement of the rotatable part 60 of the battery portion 12 around the main axis X for pressing the liquid reservoir opening element 70 against the liquid reservoir 234 housed in the cavity 240 thereby opening the liquid reservoir 234.

The heating coil 28 (not shown in FIG. 4) is arranged with respect to the liquid reservoir opening element 70 such that in the closed cavity configuration the heating coil 28 is electrically connected to the battery and the liquid reservoir opening element 70 opens, e.g. pierces, the housed liquid reservoir 234, 334, 434 in a vicinity of the connected heating coil 28 for allowing liquid from the liquid reservoir 234, 334, 434 to leak onto the heating coil 28 in case of at least a minimum pressure difference between the liquid reservoir 234, 334, 434 and the central passage 32. In some embodiments, the minimum pressure difference can be produced by a user sucking at the inhalation port 36.

In some embodiments, the liquid reservoir opening element 70 is a piercing pin comprised by the atomizer 26.

The tray 250 is part of one of the battery portion 12 and the mouthpiece portion 13. Optionally, it has a limiting element configured to interact with the one portion of the battery portion 12 and the mouthpiece portion 13 not comprising the tray 250 for limiting the movement.

Figure 5:
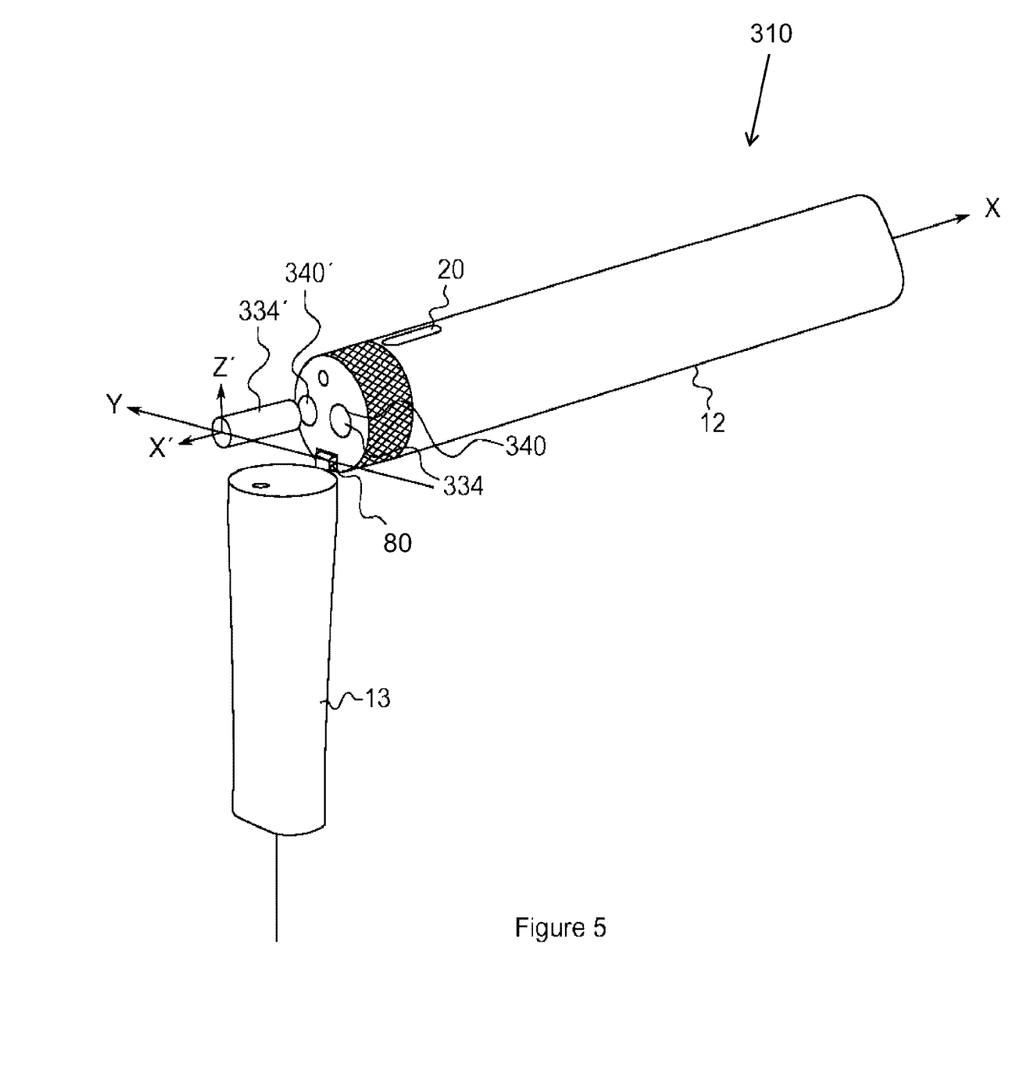
FIG. 5 shows a schematic depicting of a further exemplary embodiment of an electronic smoking device according to an aspect of the invention.

An electronic smoking device 310 according to a further exemplary embodiment of the invention is shown in FIG. 5 in the insertion configuration. Portions 12, 13 are connected by a connecting member 80 which allows for rotation around a rotation axis Y perpendicular to the main axis X. Liquid reservoirs 334 can be inserted into cavities 340, 340' and the movement comprises a rotational movement around the rotation axis Y. By a respective rotational counter-movement, the cavities 340, 340' are closed by the mouthpiece portion 13. Optionally, the rotational counter-movement also pushes the liquid reservoirs 334, 334' into the cavities 340, 340' and/or presses a liquid reservoir opening element 70, e.g. a piercing element, against the liquid reservoir 334 housed in one of the cavity 340 thereby opening, e.g. piercing or perforating) the liquid reservoir 334 housed in said one cavity 340. Alternatively, the movement further comprises a twist movement of a rotational part 60 of the battery portion 12 around the main axis X and the counter-movement further comprises a corresponding twist counter-movement for pressing a liquid reservoir opening element 70 against the liquid reservoir 334 housed in the cavity thereby opening the liquid reservoir 334.

Optionally, the electronic smoking device 310 comprises an ejecting element and the movement further causes the ejecting element to eject one, some or all liquid reservoirs housed by the cavities.

The heating coil is arranged with respect to the liquid reservoir opening element such that in the closed cavity configuration the heating coil is electrically connected to the battery and the liquid reservoir opening element opens, e.g. pierces, the liquid reservoir housed in said one cavity in a vicinity of the connected heating coil for allowing liquid from the liquid reservoir to leak onto the heating coil in case of at least a minimum pressure difference between the liquid reservoir and the central passage. In some embodiments, the minimum pressure difference can be produced by a user sucking at the inhalation port.

Figure 6:
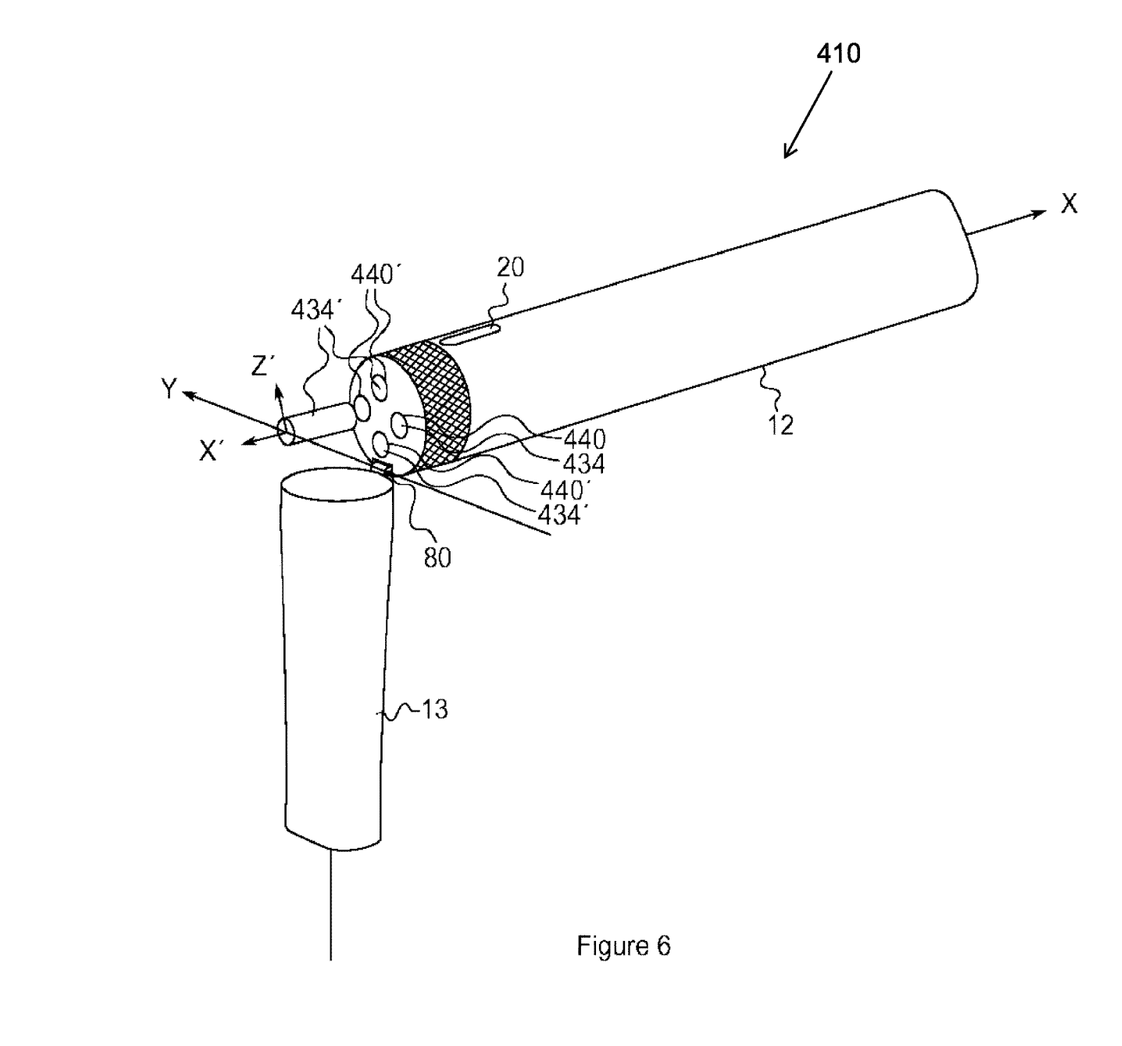
FIG. 6 shows a schematic depicting of a yet further exemplary embodiment of an electronic smoking device according to an aspect of the invention.

An electronic smoking device 410 according to a yet further exemplary embodiment of the invention is shown in FIG. 6 in the insertion configuration. Portions 12, 13 are connected by a connecting member 80 which allows for rotation around a rotation axis Y perpendicular to the main axis X. Liquid reservoirs 434, 434' can be inserted into cavities 440, 440' and the movement comprises a rotational movement around the rotation axis Y. By a respective rotational counter-movement, the cavities 440, 440' are closed by the mouthpiece portion 13. Optionally, the rotational counter-movement also pushes the liquid reservoirs 434, 434' into the cavities 440, 440' and/or presses a liquid reservoir opening element 70 against the liquid reservoir 434 housed in one of the cavity 440 thereby opening, e.g. piercing or perforating, the liquid reservoir 434 housed in said one cavity 440. Alternatively, the counter-movement further comprises a twist movement around the main axis X for pressing a liquid reservoir opening element against the liquid reservoir 234 housed in the cavity 440 thereby opening, e.g. piercing, the liquid reservoir 434.

The heating coil is arranged with respect to the liquid reservoir opening element such that in the closed cavity configuration the heating coil is electrically connected to the battery and the liquid reservoir opening element opens, e.g. pierces, the liquid reservoir housed in said one cavity in a vicinity of the connected heating coil for allowing liquid from the liquid reservoir to leak onto the heating coil in case of at least a minimum pressure difference between the liquid reservoir and the central passage. In some embodiments, the minimum pressure difference can be produced by a user sucking at the inhalation port.

Holding two liquid reservoirs within the device prolongs time duration between liquid reservoir replacements. That is, the electronic smoking device 410 according to a yet further exemplary embodiment of the invention allows, at least in the insertion configuration, the rotatable part 60 to be rotated around the main axis X, thereby enabling selection of the one cavity 440. The embodiment prolongs time intervals between necessary replacements of liquid containers 434.

In accordance with one aspect of the present invention, an electronic smoking device comprises two portions wherein one of the portions comprises a cavity configured for at least partly housing a liquid reservoir. The portions can be moved with respect to each other, by a movement and a respective counter movement, at least between an insertion configuration and a closed cavity configuration. In the insertion configuration, a liquid reservoir can be inserted into the cavity. In the closed cavity configuration, the cavity is closed by the other portion and a liquid reservoir opening element comprised by said one or the other portion opens, e.g. pierces, the housed liquid reservoir.

The movement can comprise a rotational movement around one rotation axis perpendicular to the main axis and/or a linear movement in direction of the main axis.

For increasing usability, at least one further cavity can be comprised in the device. The further cavity then is configured for at least partly housing a further liquid reservoir and the cavities are comprised in a rotatable part of the one portion. By rotating, in the insertion configuration, the rotatable part, one of the liquid reservoirs can be selected for being pierced in the closed cavity configuration. The rotatable part can be rotatable around the main axis.

For correct insertion, the cavity can be configured for receiving a corresponding liquid reservoir being asymmetric at least with respect to one axis.

For ease of insertion, the corresponding liquid reservoir is further axially symmetric with respect to a symmetry axis perpendicular to the one axis. In the closed cavity configuration, the one axis of the housed liquid reservoir can be perpendicular to the main axis, for instance.

For locking, the movement can comprise a twist movement around the main axis of the electronic smoking device.

For ease of insertion, the cavity can comprise a tray.

For ease of liquid reservoir replacement, the movement can comprise a linear movement along the main axis.

Also for ease of liquid reservoir replacement, the electronic smoking device can be configured such that, by the movement, an ejection force can be applied on the housed liquid reservoir, the force ejecting the liquid reservoir at least partly out of the cavity.

The two portions can comprise a battery portion for comprising a battery and a mouthpiece portion comprising an inhalation port.

A heating coil can be arranged in a central passage of the electronic smoking device, the central passage connecting an air inlet port of the electronic smoking device with the inhalation port. Then, the heating coil is arranged with respect to the liquid reservoir opening element such that in the closed cavity configuration the heating coil is electrically connected to the battery and the liquid reservoir opening element opens, e.g. pierces, the housed liquid reservoir in a vicinity of the connected heating coil for allowing liquid from the liquid reservoir to leak onto the heating coil in case of at least a minimum pressure difference between the liquid reservoir and the central passage.

In some embodiments, the minimum pressure difference can be produced by a user sucking at the inhalation port. In some embodiments, the cavity is configured for housing only a part of the liquid reservoir and the other portion comprises at least one corresponding cavity for housing a remaining part of the liquid reservoir.

In some embodiments the electronic smoking device comprises a control element, e.g. a printed circuit board (PCB), wherein, at least in the closed cavity configuration, the electronics of the liquid reservoir contact the control element, thereby enabling an interfacing, e.g. via a microswitch, of the control element with the electronics. An advantage thereof is enablement of improved control strategy.

In some aspects, the invention concerns the power supply/atomizer portion comprising a liquid reservoir portion detection element and an activation element. In some embodiments, the liquid reservoir portion detection element, which exemplarily has the form of a pin, is moveable between a first default position and a second, pushed back position, for instance by said movement for achieving the closed cavity configuration. The activation element, which can be configured as a simple micro switch, is adapted to be operated by the liquid reservoir portion detection element when the liquid reservoir portion detection element is moved from the first position to the second position. A resilient element, e.g. a spring, is adapted to push the liquid reservoir portion detection element toward of the first position. The resilient element is coupled with the liquid reservoir portion detection element. The resilient element, the liquid reservoir portion detection element, and the activation element also form part, on the side of the power supply/atomizer portion, of a liquid reservoir portion detection device according to an aspect of the invention.

The liquid reservoir portion detection device serves to detect, in the power supply/atomizer portion, the coupling of a new, intact liquid reservoir portion with the power supply/atomizer portion. In an e-cigarette, a liquid reservoir portion has to be replaced by a new liquid reservoir portion in case the liquid reservoir becomes empty. As described below, a coupling of a new, intact liquid reservoir portion with the power supply/atomizer portion can simply and reliably be detected.

Once a liquid reservoir portion with the empty liquid reservoir has already been removed from the power supply/atomizer portion and a new, intact liquid reservoir portion is provided, an opening of the respective liquid reservoir that faces the power supply/atomizer portion is covered by the foil and the opening of cavity at the same end of the liquid reservoir portion is blocked by means of the engaging element. In corresponding embodiments of the invention, the engaging element is a cover element that completely covers the opening of the cavity. Other embodiments comprise alternative engaging elements which e.g. do not completely cover the opening of the cavity but only partly block the respective opening.

In some embodiments, while coupling the new liquid reservoir portion with the power supply/atomizer portion, the liquid reservoir portion is slidably fitted onto the power supply/atomizer portion. As a coupling interface, a simple push fit is used in the example. Alternative ways of coupling the respective portions have already been mentioned above. A one-way design of the interface facilitates the coupling process and helps to prevent misalignment of the power supply/atomizer portion and the liquid reservoir portion.

While pushing the liquid reservoir portion onto the power supply/atomizer portion, on the one hand, as already mentioned above, the piercing portion of the atomizer pierces the foil that covers the liquid reservoir. On the other hand, the liquid reservoir portion detection element of the power supply/atomizer portion contacts and engages with the engaging element of the liquid reservoir portion. The engaging element is basically configured to be destructible upon a pressure load applied by the liquid reservoir portion detection element, which pressure load is above a predetermined value. Due to the fact, however, that the engaging element is adapted, before being destructed, to withstand a pressure load that is exerted by the liquid reservoir portion detection element, which pressure load is sufficiently high so as to move the liquid reservoir portion detection element from the first position toward the second position against the pressure load provided by the resilient element, the liquid reservoir portion detection element is moved from the first, default position in which the resilient element is essentially stressfree to the second, pushed back position in which the resilient element is at least partially compressed. While being moved from the first position to the second position, the liquid reservoir portion detection element operates the activation element. An activation signal generated by the activation element indicates the coupling of a new, intact liquid reservoir portion. This activation signal can be processed by the control electronics. In order to indicate the coupling to a user of the smoking device, the control electronics can cause an LED to light up according to a predetermined illuminating pattern. In particular, the control electronics, when receiving the activation signal, can reset the first dose counter that currently stores the puffing time since the most recent replacement of a liquid reservoir portion.

According to other embodiments, the control electronics is configured to temporarily deactivate the e-cigarette when the first dose counter that stores the puffing time since the most recent replacement of a liquid reservoir portion exceeds a first predefined threshold value. This ensures that the risk of harmful vaporizations products is mitigated which may occur in case the atomizer runs dry. By coupling a new liquid reservoir portion to the power supply/atomizer portion, thereby providing new liquid, the respective dose counter can be reset as described above.

According to yet another embodiment, the control electronics is configured to permanently deactivate the e-cigarette when the second dose counter that stores total puffing time, i.e. the puffing time since the bringing into service of the power supply/atomizer portion, exceeds a second predefined threshold value. This ensures that the risk of harmful vaporizations products is mitigated which may also occur when the atomizer has been used for a long time (i.e. longer than the second predefined threshold).

Both the first and the second dose counters can be implemented in software.

When the new liquid reservoir portion is finally fitted onto the power supply/atomizer portion, the engaging element is destructed upon further engagement with the liquid reservoir portion detection element and the respective pressure load applied by liquid reservoir portion detection element. In exemplary embodiments, the liquid reservoir portion detection element is a pin having a tip portion which is adapted to pierce, and thereby destruct the cover element during the coupling of the liquid reservoir portion with the power supply/atomizer portion. Because the destructed engaging element can no longer withstand the pressure load provided by the resilient element, the liquid reservoir portion detection element is again moved from the second position to the first, default position. In this position, the liquid reservoir portion detection element is prepared to detect the coupling of a new, intact liquid reservoir portion to the power supply/atomizer portion. In the state, in which the liquid reservoir portion is coupled to the power supply/atomizer portion, the liquid reservoir portion detection element extends into the formerly empty cavity of the liquid reservoir portion. In other words, in the coupled state, the cavity receives at least part of the liquid reservoir portion detection element.

Due to the fact that the engaging element is destructed in the final phase of the coupling process, after the activation signal has been generated by the activation element, an erroneous reuse of an old liquid reservoir portion, i.e. a liquid reservoir portion with an empty or at least already opened liquid reservoir, can indirectly be prevented. This is because in an old, i.e. pre-used liquid reservoir portion the engaging element is already destructed. Consequently, when coupling such a pre-used liquid reservoir portion to the power supply/atomizer portion, the liquid reservoir portion detection element is not moved from the first position to the second position and—due to that lack of a respective intact engaging element—the activation element is not operated, no activation signal is generated and the first dose counter that stores the puffing time since the most recent replacement of a liquid reservoir portion is not reset. As soon as this first dose counter exceeds the above mentioned first predefined threshold, the e-cigarette will temporarily be deactivated, thereby indirectly indicating that the recently coupled liquid reservoir portion was not a new, intact liquid reservoir portion. In addition, a destructed engaging element, e.g. a pierced cover element, can readily be recognized by the user, and also in this way prevent a potential reuse of a liquid reservoir portion.

An exemplary embodiment of the liquid reservoir portion comprises a combined foil element. This foil element, which is intended to be heat-sealed onto the liquid reservoir portion, includes a first foil element that is adapted to cover and seal the liquid reservoir portion and a second foil element that is adapted to cover the opening of the cavity. An air duct, which ends in the inhalation port, remains uncovered. According to this configuration, the exposure of the liquid to possible contaminants is significantly reduced as the liquid is only in contact with the material of the liquid reservoir portion and the cover foil. The fact that a cover foil can be used as an engaging element in the context of a liquid reservoir portion detection device has already been described above.

In another exemplary embodiment of the liquid reservoir portion, the engaging element is configured as a small plate which is fixed to the boundary of the opening of the cavity by means of three predetermined breaking points. The plate and the connection to the boundary of the opening via the predetermined breaking points are configured, on the one hand, to withstand a pressure load that is exerted by the liquid reservoir portion detection element, e.g. a pin, which pressure load is sufficiently high so as to move the liquid reservoir portion detection element from the first position toward the second position against the pressure load provided by the resilient element. On the other hand, the connection is configured to break, resulting in a destructed engaging element, in the final phase of coupling the respective liquid reservoir portion with a power supply/atomizer portion. Of course, the geometric form (triangle) and the number of predetermined breaking points can vary, as long as the plate functions as an engaging element as generally described above.

Yet another exemplary embodiment of the liquid reservoir portion comprises the engaging element provided by a thread which is configured to break in case a pressure load applied is too high.

An exemplary corresponding liquid reservoir portion detection element includes a hook-like end portion that is adapted to engage with the tread in order to move the liquid reservoir portion detection element, in the second phase of a connection process from the first position to the second position.

While this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims.

LIST OF REFERENCE SIGNS 10, 210, 310, 410 electronic smoking device
12 battery portion
13 mouthpiece portion
14 atomizer/liquid reservoir portion
16 end cap
18 battery
20 light-emitting diode (LED)
22 control electronics
24 airflow sensor
26 atomizer
28 heating coil
30 wick
32 central passage
34, 234, 234', 334,
334', 434, 434' liquid reservoir
36 air inhalation port
38 air inlets
60 rotatable part
240, 340, 340',
440, 440' cavity
70 liquid reservoir opening element
80 connecting element
X longitudinal main axis
Y perpendicular axis
X' symmetry axis of liquid reservoir
Z' one axis of liquid reservoir perpendicular to X'

The invention claimed is:

1. An electronic smoking device comprising:
   two portions wherein one of the portions includes
     a cavity configured for at least partly housing a liquid reservoir; and
   wherein the portions are configured to move with respect to each other, by a movement and a respective counter movement, at least between
     an insertion configuration in which the liquid reservoir is inserted into the cavity, and
     a closed cavity configuration in which the cavity is closed by the other portion and a liquid reservoir opening element including said one or the other portion that is configured to open the housed liquid reservoirs;
   wherein the portions are further configured such that, by the movement, an ejection force is applied on the housed liquid reservoir, the force ejecting the liquid reservoir at least partly out of the cavity.

2. The electronic smoking device of claim 1, wherein the movement is a rotational movement around a rotation axis perpendicular to a longitudinal main axis of the electronic smoking device.

3. The electronic smoking device of claim 2, further including at least one further cavity configured for at least partly housing a further liquid reservoir, wherein the cavities are comprised in a rotatable part of the one portion, and wherein by rotating the rotatable part, in the insertion configuration and with respect to the one portion, one of the liquid reservoirs is configured to be selected for being pierced in the closed cavity configuration.

4. The electronic smoking device of claim 3, wherein the rotatable part is rotatable around the longitudinal main axis.

5. The electronic smoking device of claim 2, wherein the cavity is configured for receiving a corresponding liquid reservoir being asymmetric at least with respect to an axis of the liquid reservoir that is perpendicular to the longitudinal main axis.

6. The electronic smoking device of claim 5, wherein the corresponding liquid reservoir is further axially symmetric with respect to a symmetry axis perpendicular to the axis of the liquid reservoir that is perpendicular to the longitudinal main axis.

7. The electronic smoking device of claim 2, wherein the movement is a twist movement around the longitudinal main axis of the electronic smoking device.

8. The electronic smoking device of claim 2, wherein the movement comprises a linear movement along the longitudinal main axis.

9. The electronic smoking device of claim 1, wherein the cavity comprises a tray.

10. The electronic smoking device of claim 1, wherein the two portions include a battery portion for housing a battery and a mouthpiece portion with an inhalation port.

11. The electronic smoking device of claim 10, further including a heating coil arranged in a passage of the electronic smoking device, the passage connecting an air inlet port of the electronic smoking device with the inhalation port, and
   wherein the heating coil is arranged with respect to the liquid reservoir opening element such that, in the closed cavity configuration, the heating coil is electrically connected to the battery, and the liquid reservoir opening element is configured to open the housed liquid reservoir in a vicinity of the connected heating coil to allow liquid from the liquid reservoir to leak onto the heating coil in response to at least a minimum pressure difference between the liquid reservoir and the passage.

12. The electronic smoking device of claim 11, wherein the minimum pressure difference is produced in response to a user drawing air through the air inhalation port.

\* \* \* \* \*